United States Patent [19]

Herschler

[11] Patent Number: 4,997,823

[45] Date of Patent: Mar. 5, 1991

[54] ANTI-INFECTIVE INJECTABLE FORMULATIONS

[75] Inventor: Richard C. Herschler, Los Altos, Calif.

[73] Assignee: Syntex (U.S.A.) Inc., Palo Alto, Calif.

[21] Appl. No.: 75,174

[22] Filed: Jul. 20, 1987

Related U.S. Application Data

[63] Continuation-in-part of Ser. No. 830,389, Feb. 18, 1986, abandoned.

[30] Foreign Application Priority Data

Feb. 17, 1987 [EP]  European Pat. Off. ........ 87102214.1

[51] Int. Cl.$^5$ ..................... A61K 37/00; A61K 31/65; A61K 31/56; A61K 31/19
[52] U.S. Cl. ........................................ 514/154; 514/2; 514/171; 514/573
[58] Field of Search ................... 514/154, 573, 171, 2

[56] References Cited

U.S. PATENT DOCUMENTS

| | | | |
|---|---|---|---|
| 3,174,899 | 3/1965 | Abramo et al. | 514/154 |
| 3,296,073 | 1/1967 | Fahey et al. | 514/154 |
| 3,549,751 | 12/1970 | McBride et al. | 514/154 |
| 3,985,791 | 10/1976 | Muchowski et al. | 560/55 |

FOREIGN PATENT DOCUMENTS

| | | | |
|---|---|---|---|
| 0150732 | 8/1985 | European Pat. Off. | 514/573 |
| 0234481 | 9/1987 | European Pat. Off. | |
| 1166732 | 2/1967 | United Kingdom | |

*Primary Examiner*—Douglas W. Robinson
*Attorney, Agent, or Firm*—Carol J. Roth; Derek Freyberg; Tom M. Moran

[57] ABSTRACT

Infection associated with parenteral injections of parenterally suitable compounds, especially of $F_{2\alpha}$ prostaglandins, is prevented by novel compositions comprising such compounds, a locally effective amount of an antibiotic, and a pharmaceutically acceptable carrier.

24 Claims, No Drawings

ANTI-INFECTIVE INJECTABLE FORMULATIONS

BACKGROUND OF THE INVENTION

Related Application

This application is a continuation-in-part of U.S. Ser. No. 830,389, filed Feb. 18, 1986, now abandoned, incorporated herein by reference.

FIELD OF THE INVENTION

This invention relates to methods for preventing infection associated with subcutaneous or intramuscular injection of mammals with parenteral formulations, especially prostaglandin formulations, and new compositions containing parenterally administrated compounds with a locally effective amount of an antibiotic.

Related Disclosure

It is frequently desirable to administer compounds to livestock by parenteral injection. For example, vaccines, hormones, vitamins and nutritional supplements are frequently administered by intramuscular injection.

$PGF_{2\alpha}$ and $PGF_{2\alpha}$ derivatives are useful for controlling the reproductive cycles of female mammals. For example, methyl $(\pm)$-$9\alpha,11\alpha,15\alpha$-trihydroxy-16-phenoxy-17,18,19,20-tetranorprosta-4,5,13-(E)-trienoate (known generically as fenprostalene) is used to induce estrus, abortion, or parturition in female mammals, particularly horses, cattle, and swine. Fenprostalene is described in U.S. Pat. No. 3,985,791, which is incorporated herein by reference in its entirety. $PGF_{2\alpha}$ and its derivatives are most commonly administered via subcutaneous or intramuscular injection.

However, due to the non-sterile conditions under which livestock are usually treated, this method of administration carries some risk of infection. Administration is most commonly performed in areas which are far from aseptic, and parenteral injection can carry normally harmless bacteria through the subject's hide where it may cause serious infection. Typically, a single implanting gun or injector is used on a large number of animals, such that infection may be spread from subject to subject.

It has now been discovered that one may prevent such infection by incorporating a small amount of an antibiotic in the injection formulation. Surprisingly, the amount of antibiotic required is far less than the usual systemic dosage.

SUMMARY OF THE INVENTION

One aspect of the invention is a composition suitable for parenteral injection in birds or mammals, which composition comprises an effective amount of a parenterally suitable compound, a locally effective amount of an antibiotic, and a pharmaceutically acceptable carrier.

Another aspect of the invention is a composition suitable for parenteral injection for inducing estrus in a female mammal, or abortion or parturition in a pregnant mammal, which composition comprises an effective amount of a $PGF_{2\alpha}$ derivative, a locally effective amount of an antibiotic, and a pharmaceutically acceptable carrier.

Another aspect of the invention is a kit for the preparation of a composition of the invention prior to injection.

Another aspect of the invention is the method for inducing estrus, abortion, or parturition in a female mammal, which method comprises administering a composition comprising an effective amount of a $PGF_{2\alpha}$ derivative, a locally effective amount of an antibiotic, and a pharmaceutically acceptable carrier.

Another aspect of the invention is the method of administering a parenterally suitable compound while preventing simultaneous infection, by including in the parenterally administered formulation a locally effective amount of an antibiotic.

DETAILED DESCRIPTION AND PREFERRED EMBODIMENTS

One aspect of the invention is a composition for parenteral administration to a mammal, which comprises a parenterally suitable compound, a locally effective amount of an antibiotic, and a pharmaceutically acceptable carrier, especially where said parenterally suitable compound is a vaccine, a hormone, a vitamin, or nutritional supplement, particularly a prostaglandin or prostacyclin, or a derivative or analog thereof. A preferred sub-genus of the invention is a composition suitable for intramuscular administration to a female mammal, which composition comprises an effective amount of a $PGF_{2\alpha}$ derivative, a locally effective amount of an antibiotic, and a pharmaceutically acceptable carrier, especially where said $PGF_{2\alpha}$ derivative is fenprostalene and said antibiotic is oxytetracycline. A preferred class of the invention is the composition wherein said fenprostalene is present in an amount between about 0.25 mg/mL and about 1.0 mg/mL, preferably about 0.5 mg/mL. A preferred sub-class of the invention is the composition in which said oxytetracycline is present in an amount between about 0.4% and about 3.2%, preferably present in an amount between about 0.4% and about 1.6%, most preferably about 1.6%. A presently preferred embodiment of the invention is the composition comprising

| fenprostalene | 0.025%–0.1% |
| oxytetracycline | 0.4%–3.2% |
| dl-α-tocopherol | 0.025%–0.050% |
| PEG 400 qs | 100.0%. |

Another aspect of the invention is a kit for the preparation of the composition of the invention prior to injection. A preferred sub-genus is the kit which comprises two containers: a first container containing a parenterally suitable compound in admixture with a pharmaceutically acceptable carrier, and a second container containing an antibiotic in admixture with a pharmaceutically acceptable carrier, wherein said parenterally suitable compound and said antibiotic are provided in such proportions that the contents of said containers when combined provide a composition of the invention. A preferred class of the invention is the kit wherein said parenterally suitable compound is fenprostalene and said antibiotic is oxytetracycline. A presently preferred embodiment is the kit wherein said first container contains a formulation comprising

| fenprostalene | 0.025%–0.10% |
| dl-α-tocopnerol | 0.025%–0.05% |
| EG 400 qs | 100.0%. | and said second container contains a formulation comprising Liquamycin ® LA-200. A presently preferred subclass of the invention is the kit which comprises a first container containing from about 1 mL to about 40 mL of a first formulation comprising about 0.1 mg/mL fenprostalene, about 0.1 mg/mL dl α-tocopherol, and PEG 400 (polyethylene glycol 400); and a second container containing from about 0.005 to about 2 mL Liquamycin® LA-200. A presently preferred embodiment is the kit which comprises a first container containing about 10 mg fenprostalene, about 10 mg dl α-tocopherol, and about 20 mL PEG glycol 400; and a second container containing about 0.8 mL Liquamycin® LA-200.

Another aspect of the invention is a method for administering parenterally suitable compounds without injection-associated infection, which method comprises administering a composition comprising a parenterally suitable compound, a locally effective amount of an antibiotic, and a pharmaceutically acceptable carrier. A preferred sub-genus of the invention is the method wherein said parenterally suitable compound is a vaccine, hormone, vitamin or nutritional supplement.

Another aspect of the invention is the method for inducing estrus, abortion, or parturition in a female mammal without initiating infection, which method comprises administering an effective amount of a $PGF_{2\alpha}$ derivative, a locally effective amount of an antibiotic, and a pharmaceutically acceptable carrier, especially where said $PGF_{2\alpha}$ derivative is fenprostalene and said antibiotic is oxytetracycline. A preferred subgenus of the invention is the method wherein said fenprostalene is present in an amount between about 0.025% and about 0.050%, preferably about 0.050%. A preferred class of the invention is the method in which said oxytetracycline is present in an amount between about 0.4% and about 3.2%, preferably about 1.6%.

The locally effective amount of antibiotic necessary to prevent injection-associated infection may be determined by one of ordinary skill by routine experimentation. For example, one may inject guinea pigs with a composition containing a test amount of antibiotic and a lethal dose of bacteria to determine the amount of antibiotic necessary. The dose of bacteria used may be a combination of several strains, or may be a representative strain such as *Clostridium chauveoi*. The amount of antibiotic required will be independent of the species of subject mammal, but may be dependent on the species of bacteria. Thus, experiments with small laboratory animals are sufficient to establish dosages for larger animals. The use of a large excess (e.g., 10 times the lethal dose when administered without an antibiotic) of lethal bacteria is sufficient to compensate for any variation due to differences in bacterial species.

DEFINITIONS

The term "antibiotic" as used herein includes all commonly used bacteriostatic and bactericidal antibiotics, which are suitable for parenteral injection. Antibiotics include without limitation aminglycosides, such as amikacin, gentamicin, kanamycin, neomycin, streptomycin, and tobramycin; cephalosporins, such as cefamandole, cefazolin, cephalexin, cephaloglycin, cephaloridine, cephalothin, cephapirin, and cephradine; macrolides, such as erythromycin and troleandomycin; penicillins, such as penicillin G, amoxicillin, ampicillin, carbenicillin, cloxacillin, dicloxacillin, methicillin, nafcillin, oxacillin, phenethicillin, and ticarcillin; polypeptide antibiotics, such as bacitracin, colistimethate, colistin, polymyxin B; tetracyclines, such as chlortetracycline, demeclocycline, doxycycline, methacycline, minocycline, tetracycline, and oxytetracycline; and miscellaneous antibiotics such as chloramphenicol, clindamycin, cycloserine, lincomycin, rifampin, spectinomycin, vancomycin, and viomycin. Additional antibiotics are described in "Remington's Pharmaceutical Sciences," 16th Ed., (Mack Pub. Co., 1980), pp. 1121-1178. Presently preferred antibiotics are penicillin, tetracycline, and oxytetracycline, particularly oxytetracycline. Recommended systemic doses of oxytetracycline for intramuscular injection in animals range from about 6.5 mg/Kg to about 20 mg/Kg.

The term "Liquamycin® LA-200" refers to an injectible oxytetracycline formulation containing about 200 mg/mL oxytetracycline. Liquamycin® LA-200 is commercially available from Pfizer.

The term "parenterally suitable compound" refers to compounds which are commonly administered by subcutaneous or intramuscular injection. Parenterally suitable compounds include, without limitation, vaccines, hormones, vitamins, nutritional supplements, and the like. Preferred parenterally suitable compounds are steroid hormones and prostaglandin derivatives, especially $PGF_{2\alpha}$ and its derivatives.

The term "PEG" refers to polyethylene glycol, which is widely available from commercial sources.

The term "$PGF_{2\alpha}$ derivative" refers to prostaglandin $F_{2\alpha}$ and prostaglandin derivatives with activity similar to prostaglandin $F_{2\alpha}$ (also known as dinoprost). $PGF_{2\alpha}$ derivatives are currently used to modulate reproductive function in female mammals, e.g., to induce estrus, parturition and abortion. Presently preferred $PGF_{2\alpha}$ derivatives are compounds of formula 1:

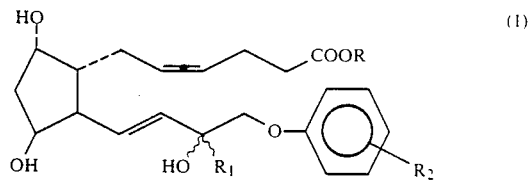

(1)

or a pharmaceutically acceptable salt thereof, wherein
R is hydrogen or lower alkyl;
$R_1$ is hydrogen, methyl, or ethyl;
$R_2$ is hydrogen, halo, trifluoromethyl, lower alkyl or lower alkoxy.

The term "lower alkyl" refers to a straight or branched saturated monovalent hydrocarbon radical containing four carbon atoms or less, for example, methyl, ethyl, n-propyl, isopropyl, n-butyl, s-butyl, i-butyl, and t-butyl.

The term "lower alkoxy" refers to a radical of the form RO—, where R is lower alkyl as defined above.

The term "halo" refers to fluoro, chloro, bromo, and iodo.

The term "effective amount" as used herein refers to the amount of parenterally suitable compound necessary to obtain the effect for which it is administered. For example, an effective amount of a $PGF_{2\alpha}$ derivative is the amount needed to effect induction of estrus, abortion, or parturition in a female mammal. As $PGF_{2\alpha}$ derivatives are known and used in the art, the effective amount of any particular $PGF_{2\alpha}$ derivative will be known or readily determined by the practitioner of ordinary skill. In general terms, an effective amount of fenprostalene for induction of parturition, for induction of estrus, or for induction of abortion is from about 0.0022 mg/Kg to about 0.011 mg/Kg, preferably from about 0.0022 mg/Kg to about 0.0044 mg/Kg, and most preferably about 0.0033 mg/Kg. The exact dosage may vary with the species of mammal and the condition being treated. However, such variations are readily calculated by one of ordinary skill.

The term "locally effective amount" refers to the quantity of antibiotic required to prevent infection associated with intramuscular injection without providing a systemic effect. Thus, a locally effective amount is less than the usual dose prescribed for systemic treatment of infection, and is preferably 10% or less of the recomended systemic dose. For example, oxytetracycline is normally prescribed for mammals in doses of about 11 mg/Kg per day (i.m.), whereas the dosage administered in the practice of the invention can be less than about 0.20 mg/Kg per injection. A locally effective amount of oxytetracycline for prevention of infection associated with intramuscular injection ranges from about 0.018 mg/Kg to about 0.14 mg/Kg, preferably from about 0.025 mg/Kg to about 0.14 mg/Kg, and most preferably about 0.03 mg/Kg. In any case, a locally effective amount is less than about 1.0 mg/Kg. As the amount is intended to be sub-systemic, the locally effective amount is more or less independent of the subject animal size. In a presently-preferred embodiment, a formulation of the invention containing about 16 mg (in 2 mL) is administered to cattle weighing about 300 Kg, for a resulting dosage of 0.05 mg/Kg.

The term "pharmaceutically acceptable acid addition salts" refers to salts of the subject compounds which possess the desired pharmacological activity and which are neither biologically nor otherwise undesirable. These salts are formed with inorganic acids such as hydrochloric acid, hydrobromic acid, sulfuric acid, nitric acid or phosphoric acid; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The term "mammal" as used herein refers to mammals such as cattle, horses, swine, sheep, goats, dogs, cats, and the like.

All percentages used herein are "weight/weight" percentages (w/w).

The term "parenteral injection" as used herein refers to administration by injection, particularly by subcutaneous or intramuscular injection.

ADMINISTRATION AND FORMULATION

One aspect of the present invention relates to pharmaceutical compositions useful for inducing estrus or parturition in female mammals, comprising an effective amount of a compound of $PGF_{2\alpha}$ derivative and a sub-systemic infection-protecting amount of an antibiotic, in admixture with a pharmaceutically acceptable non-toxic carrier. An effective amount of a $PGF_{2\alpha}$ derivative is that amount which is necessary to induce estrus in a female mammal, or the amount necessary to induce parturition in a pregnant mammal near the end of that mammal's gestation period.

Useful pharmaceutical carriers for the preparation of the pharmaceutical compositions hereof are liquids and solids, and can take the form of solutions, suspensions, elixirs, tablets, pills, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers. Other suitable pharmaceutical carriers and their formulations are described in "*Remington's Pharmaceutical Sciences*" by E. W. Martin.

The compositions of the invention are prepared in solution form using standard techinques. $PGF_{2\alpha}$ derivatives are available from commercial sources, or may be prepared by the methods taught in the art. It is preferred to include a small amount of an anti-oxidizing agent such as dl-α-tocopherol in the formulation to protect the prostaglandin from oxidation. Antibiotics are also available from commercial sources.

The compositions of the invention may be assayed for efficacy by injecting suitable test animals with mixtures of compositions of the invention and lethal doses of infectious bacteria of a type commonly found on animal hide. For example, *Clostridium chauveoi* is a potentially lethal species of bacteria which may be used as a suitable challenge bacteria.

EXAMPLE 1

(Formulations)

(A) A formulation suitable for subcutaneous injection for inducing abortion, parturition, or estrus in cattle is prepared as follows:

| | |
|---|---|
| fenpostalene | 0.5 mg |
| oxytetracycline | 16.0 mg |
| dl-α-tocopherol | 0.5 mg |
| sterile EG 400   qs | 1.0 mL |

The fenprostalene and oxytetracycline are added to a solution of dl-α-tocopherol and sterile PEG 400, and the resulting solution is mixed well.

(B) A kit for preparing a multiple dose formulation suitable for subcutaneous injection for inducing abortion, parturition, or estrus in cattle is prepared as follows:

| | |
|---|---|
| Formulation A: | |
| fenprostalene | 10.0 mg |
| dl-α-tocopnerol | 10.0 mg |
| sterile EG 400   qs | 20.0 mL |
| Formulation B: | |
| Liquamycin® LA-200 (200 mg/mL oxytetracycline) | 0.8 mL |

The fenprostalene is added to a solution of dl-α-tocopherol and sterile PEG 400, and the resulting solution is mixed well to prepare the formulation for the first vial. A second vial is provided for the second formulation. Prior to administration, the contents of the second vial are added to the contents of the first vial, and the vial shaken. The resulting formulation provides about ten doses of fenprostalene.

EXAMPLE 2

(Formulations)

Other formulations suitable for intramuscular injection in cattle were prepared as follows:

| | |
|---|---|
| (A) Progesterone: | |
| progesterone | 100.0 mg |
| oxytetracycline | 16.0 mg |
| sterile water for injection   qs | 5.0 mL |
| (B) Oxytocin: | |

-continued

| purified oxytocin principle (10 U/ml) | 1.5 mL |
| --- | --- |
| oxytetracycline | 16.0 mg |
| sterile water for injection | 1.0 mL |
| (C) Cortisone acetate: | |
| cortisone acetate | 1.5 g |
| oxytetracycline | 16.0 mg |
| sterile water for injection   qs | 5.0 mL |

(D) Similarly, proceeding as in parts A–C above, one can divide the oxytetracycline dose from the other active compound, or replace the oxytetracycline dose with an equivalent amount of Liquamycin® LA-200, to prepare a two-component kit, as in Example 1(B).

EXAMPLE 3

(Guinea Pig Assay)

Nine groups of five Guinea pigs (587–720 g/animal, Biolabs) were selected at random for challenge with *Clostridium chauveoi*. A 0.5 mL (100 $LD_{50}$ per 0.5 mL dose) dose of the indicated formulation (containing PEG 400, dl-α-tocopherol, oxytetracycline, and *C. chauveoi*) was administered by intramuscular injection to the left rear leg of each animal:

| | Formulation | | | |
|---|---|---|---|---|
| Group # | *C. chauveoi* (per 1 mL) | PEG 400 (for 1 mL) | tocopherol (mg/m) | oxytetracycline (mg/mL) |
| 1 | 200 $LD_{50}$ | qs | 0.25 | 0.0 |
| 2 | 200 $LD_{50}$ | qs | 0.25 | 8.0 |
| 3 | 200 $LD_{50}$ | qs | 0.25 | 4.0 |
| 4 | 200 $LD_{50}$ | qs | 0.25 | 2.0 |
| 5 | 200 $LD_{50}$ | qs | 0.25 | 1.0 |
| 6 | 200 $LD_{50}$ | qs | 0.25 | 0.5 |
| 7 | 200 $LD_{50}$ | qs | 0.25 | 0.25 |
| 8 | 200 $LD_{50}$ | qs | 0.25 | 0.25 |
| 9 | 200 $LD_{50}$ | qs | (5% $CaCl_2$) | |

The number of animals surviving at 0, 18, 25, 42, 48, 72, and 96 hours post administration was counted and recorded. The results demonstrated that a locally effective amount of oxytetracycline was effective to prevent injection-associated infection by *C. chauveoi.*

What is claimed:

1. A composition suitable for parenteral injection in a bird or mammal selected from the group consisting of cattle, horses, swine, sheep, goats, dogs and cats, which composition comprises:

an effective amount of a parenterally suitable compound selected from the group consisting of vaccines, steroid hormones, vitamins, prostaglandin derivatives and prostacyclin derivatives;

a locally effective amount of an antibiotic; and a pharmaceutically acceptable carrier.

2. A composition suitable for parenteral injection for inducing estrus in a female mammal selected from the group consisting of cattle, horses, swine, sheep, goats, dogs and cats, or abortion or parturition in a pregnant mammal selected from the group consisting of cattle, horses, swine, sheep, goats, dogs and cats, which composition comprises:

an effective amount of a $PGF_{2\alpha}$ derivative;

a locally effective amount of an antibiotic; and a pharmaceutically acceptable carrier.

3. The composition of claim 2 wherein said $PGF_{2\alpha}$ derivative is fenprostalene and said antibiotic is oxytetracycline.

4. The composition of claim 3 wherein said fenprostalene is present in an amount between about 0.25 mg/mL and about 1.0 mg/mL.

5. The composition of claim 3 wherein said oxytetracycline is present in an amount between about 0.4% and about 3.2%.

6. The composition of claim 3 which comprises:

0.025%–0.050% fenprostalene;

0.4%–3.2% oxytetracycline; and a pharmaceutically acceptable carrier.

7. The composition of claim 6 which comprises:

0.025%–0.050% fenprostalene;

0.025%–0.050% dl-α-tocopherol;

0.4%–1.6% oxytetracycline; and a pharmaceutically acceptable carrier.

8. A method for inducing estrus, abortion, or parturition in a female mammal selected from the group consisting of cattle, horses, swine, sheep, goats, dogs and cats without initiating infection, which method comprises:

parenterally administering a composition containing an effective amount of a $PGF_{2\alpha}$ derivative; a locally effective amount of an antibiotic; and a pharmaceutically acceptable carrier.

9. The method of claim 8 wherein said $PGF_{2\alpha}$ derivative is fenprostalene and said antibiotic is oxytetracycline.

10. The method of claim 9 wherein said fenprostalene is present in an amount between about 0.25 mg/mL and about 1.0 mg/mL.

11. The method of claim 9 wherein said oxytetracycline is present in an amount between about 0.4% and about 3.2%.

12. The method of claim 9 wherein said composition comprises:

0.025%–0.050% fenprostalene;

0.4%–3.2% oxytetracycline; and a pharmaceutically acceptable carrier.

13. The method of claim 12 wherein said composition comprises:

0.025%–0.050% fenprostalene;

0.025%–0.050% dl-α-tocopherol;

0.4%–1.6% oxytetracycline; and a pharmaceutically acceptable carrier.

14. A method for administering a parenterally suitable compound to a bird or mammal selected from the group consisting of cattle, horses, swine, sheep, goats, dogs and cats without initiating infection, which method comprises:

parenterally administering a composition containing an effective amount of a parenterally suitable compound selected from the group consisting of vaccines, steroid hormones, vitamins, prostaglandin derivatives and prostacyclin derivatives; a locally effective amount of an antibiotic; and a pharmaceutically acceptable carrier.

15. A kit for the preparation of an anti-infective composition suitable for parenteral injection in a bird or mammal selected from the group consisting of cattle, horses, swine, sheep, goats, dogs and cats, which comprises:

two containers;

a first container containing a first formulation comprising a parenterally suitable compound selected from the group consisting of vaccines, steroid hormones, vitamins, prostaglandin derivatives and prostacyclin derivatives and a pharmaceutically acceptable carrier; and a second container containing a second formulation comprising an antibiotic and a pharmaceutically acceptable carrier, wherein said first formulation and said second formulation are provided in such proportions that the mixture of the formulations provides an effective amount of said parenterally suitable compound and a locally effective amount of said antibiotic.

16. The kit of claim 15 wherein said parenterally suitable compound is a $PGF_{2\alpha}$ derivative and said antibiotic is oxytetracycline.

17. The kit of claim 16 wherein said $PGF_{2\alpha}$ derivative is fenprostalene.

18. The kit of claim 17 wherein said first formulation comprises:

| fenprostalene | [0.025%–0.01%] | 0.025%–0.1% |
|---|---|---|
| dl-α-tocopherol | [0.25%–5.0%] | 0.025%–0.05% |
| PEG 400 qs | 100.0%. | | and said second formulation comprises an injectable formulation containing about 200 mg/mL oxytetracycline.

19. The kit of claim 18 which comprises:
a first container containing from about 1 mL to about 40 mL of a first formulation comprising about 0.1 mg/mL fenprostalene, about 0.1 mg/mL dl α-tocopherol, and PEG 400; and
a second container containing from about 0.005 to about 2 mL of an injectable formulation containing about 200 mg/mL of oxytetracycline.

20. The kit of claim 19 wherein
said first formulation comprises about 10 mg fenprostalene, about 10 mg dl α-tocopherol, and about 20 mL PEG 400; and
said second formulation comprises about 0.8 mL of an injectable formulation containing about 200 mg/mL oxytetracycline.

21. The kit of claim 17 wherein said first container contains from about 1 mL to about 40 mL of the said first formulation, and said second container contains from about 0.005 to about 2 mL of the second formulation.

22. The kit of claim 21 wherein said first container contains about 20 mL of said first formulation.

23. The kit of claim 22 wherein said first formulation comprises about 10 mg fenprostalene, about 10 mg dl-α-tocopherol, and PEG 400.

24. The kit of claim 23 wherein said second container contains about 0.8 mL of an injectable formulation containing about 200 mg/mL oxytetracycline.

* * * * *